(12) United States Patent
Southby et al.

(10) Patent No.: US 8,291,898 B2
(45) Date of Patent: *Oct. 23, 2012

(54) DISPENSING APPARATUS

(75) Inventors: William Southby, Norfolk (GB); Martin Swain, Norfolk (GB); Graham Hately, Norfolk (GB); Andrew Wright, Norfolk (GB)

(73) Assignee: Consort Medical PLC, Hertfordshire (GB)

( * ) Notice: Subject to any disclaimer, the term of this patent is extended or adjusted under 35 U.S.C. 154(b) by 1255 days.

This patent is subject to a terminal disclaimer.

(21) Appl. No.: 11/802,558

(22) Filed: May 23, 2007

(65) Prior Publication Data

US 2008/0017192 A1    Jan. 24, 2008

(30) Foreign Application Priority Data

May 26, 2006 (GB) .................................. 0610541.5

(51) Int. Cl.
*A61M 11/00* (2006.01)
*A61M 11/08* (2006.01)

(52) U.S. Cl. ......... 128/200.23; 128/200.14; 128/200.17; 128/203.12; 128/203.23; 128/205.23

(58) Field of Classification Search ............. 128/200.14, 128/200.18, 200.23, 203.12, 203.15, 203.23, 128/205.23; 222/32, 36, 162; 116/307–309, 116/317, 318
See application file for complete search history.

(56) References Cited

U.S. PATENT DOCUMENTS

| | | | |
|---|---|---|---|
| 3,178,110 A | 4/1965 | Knecht et al. | |
| 3,622,053 A | 11/1971 | Ryden | |
| 3,994,421 A | 11/1976 | Hansen | |
| 4,414,972 A | 11/1983 | Young et al. | |
| 4,563,574 A | 1/1986 | Dreyer et al. | |
| 4,841,964 A * | 6/1989 | Hurka et al. ............. | 128/203.15 |
| 5,522,378 A | 6/1996 | Ritson et al. | |
| 5,562,219 A * | 10/1996 | de Pous et al. ................ | 215/274 |
| 5,565,861 A | 10/1996 | Mettler et al. | |
| 5,772,080 A * | 6/1998 | de Pous et al. ............. | 222/321.7 |
| 5,808,337 A | 9/1998 | Weimer et al. | |

(Continued)

FOREIGN PATENT DOCUMENTS

CA         2 392 466 A1     6/1997

(Continued)

OTHER PUBLICATIONS

European Extended Search Report for Application No. EP 07 25 1812 dated Jul. 23, 2007.

(Continued)

*Primary Examiner* — Clinton T Ostrup
(74) *Attorney, Agent, or Firm* — Smith, Gambrell & Russell, LLP

(57) ABSTRACT

The present invention provides a dispensing apparatus for delivering metered doses of product from a pressurised dispensing container comprising:
  a housing comprising a body portion and a removable mouthpiece, the body portion containing a dose counting mechanism and a sleeve;
  the body portion comprising an aperture through which said pressurised dispensing container can pass to be received in the sleeve but through which the sleeve is unable to pass such that the sleeve is retained within the body portion;
  the sleeve being located in the body portion such that an upper end of said pressurised dispensing container when received in the sleeve is accessible to allow actuation of said pressurised dispensing container;
  the apparatus comprising means for retaining said pressurised dispensing container in the body portion.

24 Claims, 8 Drawing Sheets

U.S. PATENT DOCUMENTS

| | | | |
|---|---|---|---|
| 5,833,088 A * | 11/1998 | Kladders et al. | 215/248 |
| 5,871,007 A | 2/1999 | Clark, Jr. | |
| 5,984,122 A | 11/1999 | Barker et al. | |
| 6,189,739 B1 | 2/2001 | von Schuckmann | |
| 6,234,168 B1 | 5/2001 | Bruna | |
| 6,360,739 B1 | 3/2002 | Rand et al. | |
| 7,322,352 B2 | 1/2008 | Minshull et al. | |
| 7,448,342 B2 | 11/2008 | Von Schuckmann | |
| 7,464,708 B2 | 12/2008 | Marx | |
| 7,543,582 B2 | 6/2009 | Lu et al. | |
| 7,571,726 B2 | 8/2009 | Parker | |
| 7,587,988 B2 | 9/2009 | Bowman et al. | |
| 7,832,351 B2 * | 11/2010 | Bonney et al. | 116/311 |
| 2003/0015191 A1 | 1/2003 | Armstrong et al. | |
| 2003/0209239 A1 | 11/2003 | Rand et al. | |
| 2004/0065326 A1 | 4/2004 | MacMichael et al. | |
| 2004/0089292 A1 | 5/2004 | Pollet et al. | |
| 2004/0094147 A1 | 5/2004 | Schyra et al. | |
| 2004/0139964 A1 | 7/2004 | Langford | |
| 2004/0149773 A1 | 8/2004 | Ouyang et al. | |
| 2004/0211420 A1 | 10/2004 | Minshull et al. | |
| 2004/0222237 A1 * | 11/2004 | Blacker et al. | 222/36 |
| 2007/0181120 A1 | 8/2007 | Wright et al. | |
| 2007/0210102 A1 | 9/2007 | Stradella et al. | |
| 2007/0246042 A1 | 10/2007 | Purkins et al. | |
| 2007/0284383 A1 | 12/2007 | Wright et al. | |
| 2008/0265198 A1 | 10/2008 | Warby | |
| 2009/0139516 A1 | 6/2009 | Augustyn et al. | |

FOREIGN PATENT DOCUMENTS

| | | | |
|---|---|---|---|
| DE | 805 817 | | 5/1951 |
| DE | 1237 820 | | 3/1967 |
| DE | 27 51 045 | | 7/1978 |
| EP | 0 227 510 | | 7/1987 |
| EP | 1369139 A1 * | | 12/2003 |
| EP | 1 787 668 | | 5/2007 |
| EP | 1787668 A1 * | | 5/2007 |
| GB | 2 372 542 | | 8/2002 |
| GB | 2414187 A * | | 11/2005 |
| WO | 93/24167 | | 12/1993 |
| WO | 99/36115 | | 7/1999 |
| WO | 99/57019 | | 11/1999 |
| WO | 01/28887 | | 4/2001 |
| WO | 02/04056 | | 1/2002 |
| WO | 02/067844 | | 9/2002 |
| WO | 03/086518 | | 10/2003 |
| WO | 2004/001664 A1 | | 12/2003 |
| WO | 2004/026380 | | 4/2004 |
| WO | 2004/089451 A1 | | 10/2004 |
| WO | 2005/044354 | | 5/2005 |
| WO | 2005/060535 | | 7/2005 |
| WO | 2005/079727 | | 9/2005 |
| WO | 2005/113044 | | 12/2005 |
| WO | 2005/114563 | | 12/2005 |
| WO | WO 2005113044 A1 * | | 12/2005 |
| WO | 2006/051006 | | 5/2006 |
| WO | 2006/054083 | | 5/2006 |

OTHER PUBLICATIONS

Search Report under Section 17 for Application No. GB0411384.1 dated Aug. 27, 2004.

European Search Report for Application No. EP 09 00 8924 dated Aug. 18, 2009.

European Search Report for Application No. EP 08 00 3115 dated Feb. 18, 2009.

Search Report under Section 17 issued in GB0523716.9, dated Mar. 20, 2006.

Further Search Report under Section 17 issued in GB0523716.9, dated Sep. 19, 2006.

Search Report under Section 17 issued in GB 0813133.6, dated Aug. 22, 2008.

Search Report under Section 17 issued in GB 0813131.0, dated Aug. 26, 2008.

* cited by examiner

DISPENSING APPARATUS

This invention relates to dispensing apparatus having integral dosage counting devices which require an axial force for actuation.

It has been recognised that there is a need to provide accurate information to a user of a dose-dispensing delivery apparatus, such as a pressurised metered dose inhaler, concerning the number of doses delivered from, or remaining in, the dispensing apparatus. Without such information, there is a danger that a user will forget how many doses have been delivered and hence take a greater or fewer number of doses than are required. There is also a danger that a user may be unaware that the dispensing container of the dispensing apparatus is empty or close to empty. This is especially dangerous where the dispensing apparatus is for use in delivering medicinal compounds for the treatment of chronic or acute symptoms, for example, as in the case of a pressurised metered dose inhaler used for treating asthmatic reactions.

It is known to provide a dispensing apparatus with a dose counting device. Typically such dose courting devices are triggered by movement of the dispensing container wherein the movement either directly or indirectly provides the motive force for incrementing or decrementing the dose counting device. One issue with mechanical dose counters is that it is typically possible to remove the pressurised dispensing container from the apparatus, and in particular from the counting mechanism. There is then the possibility of actuating the pressurised dispensing container with it removed from the counting mechanism which would result in the counting mechanism effectively under-counting the true number of doses dispensed from the pressurised dispensing container. One solution to this problem is to provide a housing where the components of the housing envelop the container in situ to directly prevent removal of the container from the apparatus. However, such designs generally involve a larger number of housing components and the housing requires a greater number of disassembly and reassembly steps to initial load the pressurised dispensing container into the housing.

Mechanical dose counters can also be difficult to manufacture so that they work reliably. One problem is that a mechanical dose counter typically requires a number of components which must be accurately located relative to one another during assembly to ensure that over-counting or under-counting is not experienced. This can lead to a requirement for very strict manufacturing tolerances which can make manufacture expensive.

According to the present invention there is provided dispensing apparatus for delivering metered doses of product from a pressurised dispensing container comprising:

a housing comprising a body portion and a removable mouthpiece, the body portion containing a dose counting mechanism and a sleeve;

the body portion comprising an aperture through which said pressurised dispensing container can pass to be received in the sleeve but through which the sleeve is unable to pass such that the sleeve is retained within the body portion;

the sleeve being located in the body portion such that an upper end of said pressurised dispensing container when received in the sleeve is accessible to allow actuation of said pressurised dispensing container;

the apparatus comprising means for retaining said pressurised dispensing container in the body portion.

Advantageously, a simple mechanism is provided for retaining the pressurised dispensing container in the apparatus to prevent incorrect counting by the dose counting mechanism.

In one embodiment the means for retaining said pressurised dispensing container in the body portion comprises an opening in the body portion dimensioned to receive a valve stem of said pressurised dispensing container as an interference fit.

In this way the relatively tight fit between the valve stern of the pressurised dispensing container and the body portion helps to prevent easy removal of the pressurised dispensing container from the body portion and hence also prevents removal of the pressurised dispensing container from the sleeve.

Preferably the opening in the body portion is a part of a conduit for conveying a product dispensed from the valve stem of the pressurised dispensing container to the removable mouthpiece.

Preferably the apparatus further comprises a biasing mechanism for urging, on insertion of said pressurised dispensing container into the sleeve, said pressurised dispensing container into positive engagement with the sleeve. In this way, advantageously, there is a greater degree of certainty when assembling a dispensing assembly comprising the apparatus and a pressurised dispensing container that the container has been properly seated into the sleeve.

Preferably the biasing mechanism urges an end face of a body of the pressurised dispensing container into contact with a basal face of the sleeve. This is advantageous in ensuring not only that the pressurised dispensing container is fully engaged into the sleeve on initial assembly but also in helping to prevent mutual slippage or separation of the pressurised dispensing container and the sleeve due to the self-weight of the sleeve. In other words the biasing affect of the biasing mechanism ensures face to face contact between the basal face of the sleeve and the end face of the body of the pressurised dispensing container whatever the orientation of the assembly or stage of actuation of the assembly.

The biasing mechanism may comprise one or more flexible projections on the sleeve which are engagable with said pressurised dispensing container.

The one or more flexible projections may depend from an inner face of the sleeve and be directed towards a basal face of the sleeve.

In one example the one or more flexible projections are engagable in an undercut of said pressurised dispensing container formed by a ferrule of said pressurised dispensing container.

In another embodiment, the means for retaining said pressurised dispensing container in the body portion is dimensioning the sleeve such that an interference fit is produced between said pressurised dispensing container and the sleeve.

In another embodiment the means for retaining said pressurised dispensing container in the sleeve is a non-return feature provided on the sleeve.

The non-return feature may comprise an inwardly directed flange of the sleeve which allows said pressurised dispensing container to pass thereby on insertion of said pressurised dispensing container but acts to resist or prevent subsequent withdrawal of said pressurised dispensing container from said sleeve.

Alternatively, the non-return feature may comprise one or more inwardly directed projections which allow said pressurised dispensing container to pass thereby on insertion of said pressurised dispensing container but acts to resist or prevent subsequent withdrawal of said pressurised dispensing container from said sleeve.

The flexible portion of the sleeve may comprise a plurality of flexible fingers which are free at one end. Alternatively, the flexible portion of the sleeve may comprise a plurality of flexible fingers which are joined or formed as one with the sleeve at an upper and lower end of the fingers.

Preferably in the above embodiments a surrounding of the aperture of the body portion comprises one or more scallops which allow access to said pressurised dispensing container in order to actuate said pressurised dispensing container, but which limit the available purchase on said pressurised dispensing container. This is particularly advantageous when used in combination with the use of an interference fit between the valve stem of the pressurised dispensing container and the body portion since the available purchase on the container is insufficient for a user to be able to apply enough force to overcome the frictional engagement of the pressurised dispensing container and the opening of the outlet conduit.

Preferably the dose counting mechanism comprises indication means for displaying to a user an indication associated with the number or quantity of doses dispensed from, or the number or quantity of doses remaining in, said pressurised dispensing container.

Preferably the sleeve comprises an indexing member for advancing the dose counting mechanism on actuation of said pressurised dispensing container.

Preferably the removable mouthpiece comprises a bayonet fitting mechanism.

Preferably, the dose counting mechanism comprises one or more annular members.

Preferably the one or more annular members are orientated for rotation about the longitudinal axis of the housing.

Preferably in use, said pressurised dispensing container is received within the housing such that the one or more annular members surround said pressurised dispensing container.

The body portion may comprise a lower part and an upper part. The lower and upper parts may be initially separate to allow assembly of the apparatus including, for example, insertion of the sleeve and annular members but may then be designed to resist subsequent opening after assembly to help prevent tampering of the dosage counter mechanism or withdrawal of the pressurised dispensing container.

Preferably the body portion is formed from Polycarbonate, ABS, Polypropylene, co-polyester or HDPE.

Preferably the sleeve is formed from acetal, ABS or nylon.

The present invention also provides a dispensing assembly comprising a dispensing apparatus as described above and a pressurised dispensing container.

The dispensing apparatus may be a pharmaceutical dispensing device, such as, for example, a pulmonary, nasal, or sub-lingual delivery device. A preferred use of the dispensing apparatus is as a pharmaceutical metered dose aerosol inhaler device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl)protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, ipratropium bromide and salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, gluconate, glutamate, eglycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosate, polygalacturonate, salicylate, stearate, subacetate, succinate, sulphate, tannate, tartrate, and triethiodide, including combinations of two or more therof. Cationic salts may also be used, for example the alkali metals, e.g. Na and K, and ammonium salts and salts of amines known in the art to be pharmaceutically acceptable, for example glycine, ethylene diamine, choline, diethanolamine, triethanpolamine, octadecylamine, diethylamine, triethylamine, 1-amino-2-propanol-amino-2-(hydroxymethyl)propane-1,3-diol, and 1-(3,4-dihydroxyphenyl)-2isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and di-methyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

Rigid components of the dispensing apparatus may be formed from, for example, from polyester, nylon, acetal or similar.

In order that the invention may be fully disclosed, embodiments will now be described, by way of example, with reference to the accompanying drawings, in which.

Figure 1:
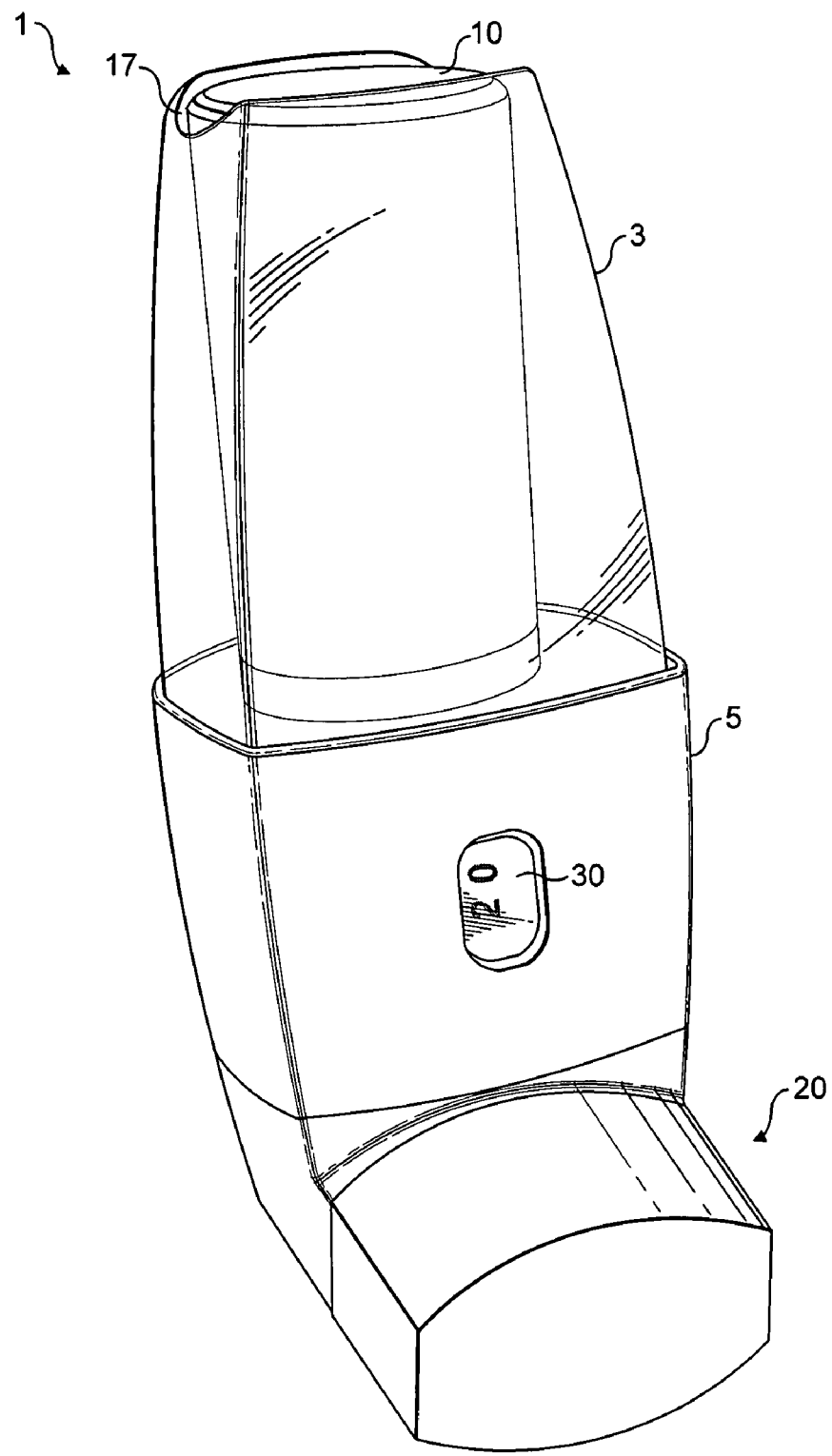
FIG. 1 is a perspective view of an embodiment of dispensing apparatus according to the present invention with a pressurised dispensing container inserted therein.
Figure 2:
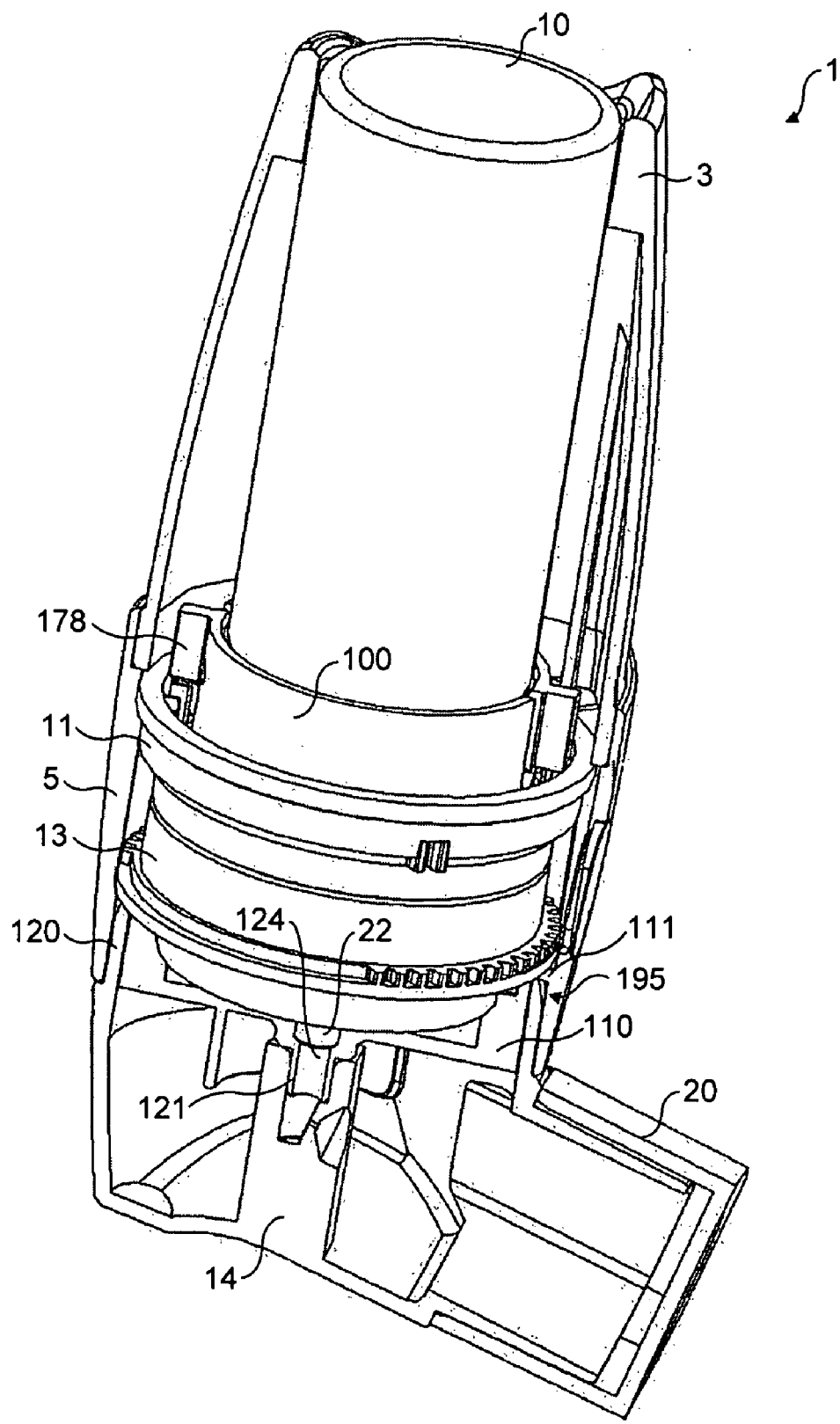
FIG. 2 is a cross-sectional view of the apparatus of FIG. 1.
Figure 8:
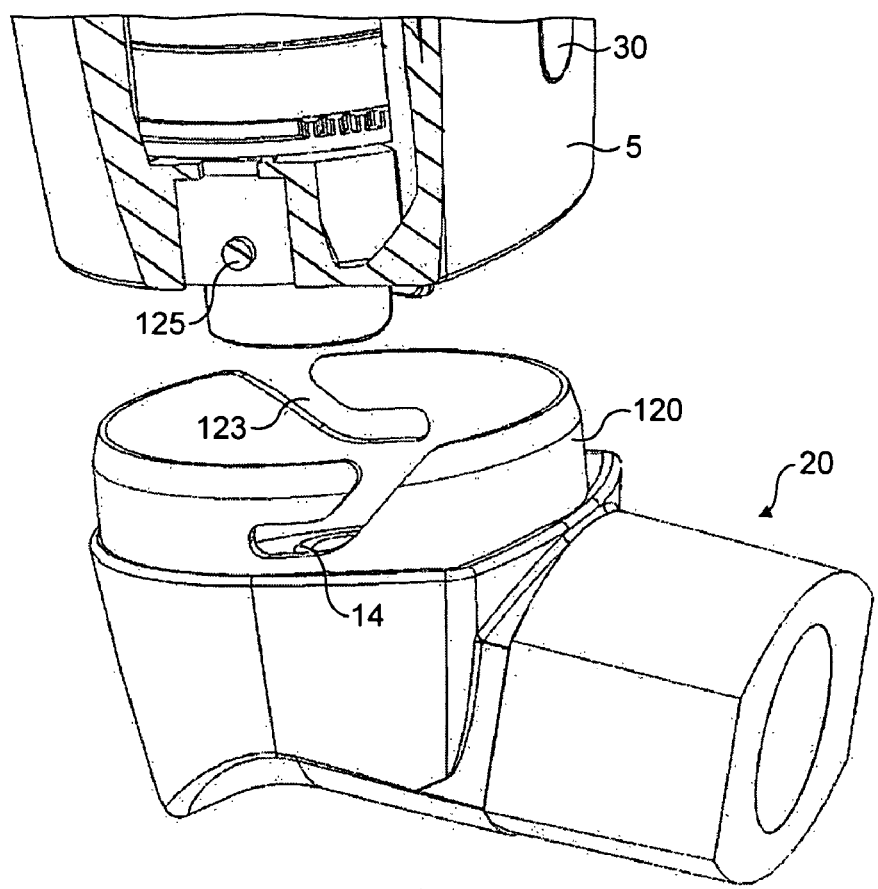
FIG. 8 is a perspective view of the dispensing apparatus of FIG. 1 with the mouthpiece detached and some parts shown in cross-section.

FIG. 1 shows a dispensing apparatus, indicated generally at 1, having a upper body 3, a lower body 5 and a detachable mouthpiece 20 shown in FIG. 8. A dust cap may be used to cover the mouthpiece 20 when the apparatus is not in use. As shown in FIG. 2, the dispensing apparatus is also provided with first and second number rings 11, 13, a cog 12 and a sleeve 100. In use the apparatus receives a pressurised dispensing container 10.

The lower body 5 is open at its upper end. The lower body 5 houses the cog 12 and the first and second number rings 11, 13. As shown in more detail in FIG. 3, the number rings 11, 13 rest upon internal projections 111 of the main body 5. Such internal projections 111 provide up-facing surfaces upon which the second number ring 13 may rest and rotate, during use. The first number ring 11 rests and rotates, during use, on top of the second number ring 13. The cog 12 is rotatably mounted within the main body 5 on a cylindrical portion 112 and interacts with both first and second number rings 11, 13. As can be seen, the axis of rotation of the cog 12 is offset from the axes of the numbered rings 11, 13 but parallel thereto so that the cog 12 can interact with both number rings 11, 13 which are housed in the substantially cylindrical part of the lower body 5 without impeding axial movement of the container 10.

The lower body 5 is provided at a lower end thereof with an axial protrusion 121 integral with the lower body 5. The axial protrusion 121 comprises a hollow elongate portion into which the valve stem 22 of the container 10 can be received as a relatively tight interference fit. The hollow portion is provided with a narrowed constriction against which the valve stem 22 can abut when the dispensing apparatus is actuated. The hollow portion forms a conduit 124 that is in fluid communication with the outlet of the valve stem of the pressurised dispensing container when the container is inserted into the apparatus. The axial protrusion 121 protrudes from the lower end of the lower body 5 as shown in FIG. 2. The axial protrusion 121 provides protection for the valve stem when the mouthpiece 20 has been removed and also directs dispensed product into the removable mouthpiece 20. In particular with the mouthpiece 20 removed the valve stem 22 is not easily accessed as it is recessed relative to the distal end of the protrusion 121. This significantly reduces the chance that the container 10 could be actuated by direct pressure being applied to the end of the valve stem 22 which might circumvent the dose counter mechanism.

The lower body 5 and upper body 3 are connectable together using co-operating formations which are push-fit together as shown in FIG. 2.

The detachable mouthpiece 20 is attached to the main body 5 by means of a bayonet fitting. As shown in FIGS. 2 and 8 the mouthpiece 20 is provided with an upstanding rim 120 in which are formed two opposed recesses 123 of roughly an L-shape configuration. The main body 5 comprises a circumferential recess 195 which receives the rim 120 when the two pieces are coupled together. At opposed points of the circumferential recess 195 the lower body 5 is provided with retaining lugs 125 which pass along the recesses 123 of the mouthpiece. Thus the mouthpiece may be coupled to the lower body 5 by locating the lugs 125 relative to the upper end of the recesses and then twisting the lower body 5 relative to the mouthpiece 20 whilst applying a compressive axial force to the two components. This results in the lugs 125 riding along the recesses resulting in the two components being firmly connected. Accordingly, it is very simple to change the mouthpiece of the dispensing apparatus, if desired or remove the mouthpiece for washing. The mouthpiece 20 is also provided with a spray block 14 for receipt of the axial protrusion 121. The spray block 14 comprises a conduit having an upper end which receives the axial protrusion 121 and a lower end which comprises a spray outlet directed towards the outlet of the mouthpiece 20. The spray outlet may be provided with a suitably dimensioned orifice or spray pattern block as known in the art to produce an atomised spray of product on dispensation.

Figure 7:
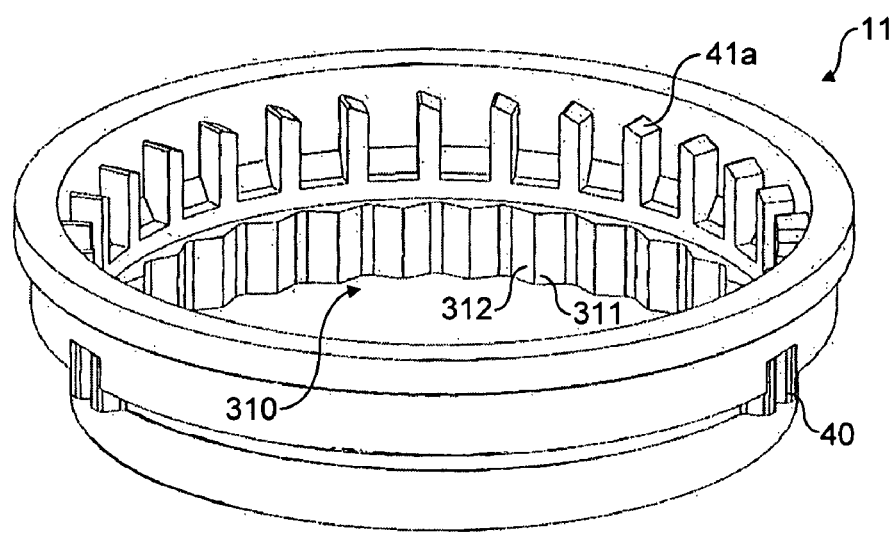
FIG. 7 is a perspective view of a first number ring having two different diameter portions, forming part of the dispensing apparatus of FIG. 1.

The first number ring 11 is provided with an upper row of angled abutment surfaces 41a located on a larger diameter portion of that number ring as shown in FIG. 7. A lower set of angled abutment surfaces are formed on a smaller diameter portion of the ring in the form of a series of inwardly directed projections 310 having a triangular cross-section when viewed from above. The projections 310 are arranged around the circumference of the lower portion of the ring 11 so as to form a series of interspersed peaks and troughs. Each projection 310 comprises two faces 311, 312 on either side of the peak. Preferably, the faces 311, 312 are arranged symmetrically about the peak. The faces 311 and 312 form angled abutment surfaces which engage the outward projection 304 of the tension arm 300 in use as will be described below.

The first number ring 11 comprises at least one notch 40 positioned on the outer edge thereof. The first number ring 11 is also provided with a set of numbering (not shown in the drawings) from 0 to 9 for each notch 40, so that after the ninth actuation of the apparatus 1, the notch 40 is in position to interact with the cog 12. In a preferred embodiment, the number ring 11 will have three notches 40 and, so, will have three sets of numbering from 0 to 9.

Figure 4:
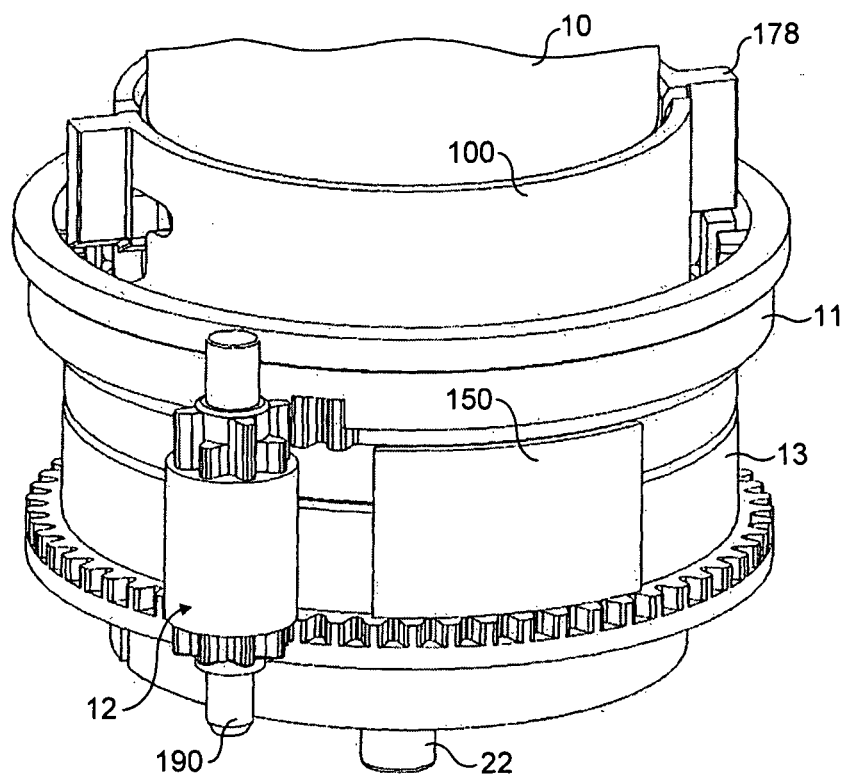
FIG. 4 is a perspective view of first and second number rings and the cog forming part of the dispensing apparatus of FIG. 1.

The second number ring 13 is provided with an extended portion 150, as shown in FIG. 4, which is positioned to enable covering of the markings on the first number ring 11 when a container locatable in the housing is empty. Advantageously, the extended portion 150 provides a clear indication to a user that the dispensing apparatus has provided its full-quota of dispensations.

Figure 3:
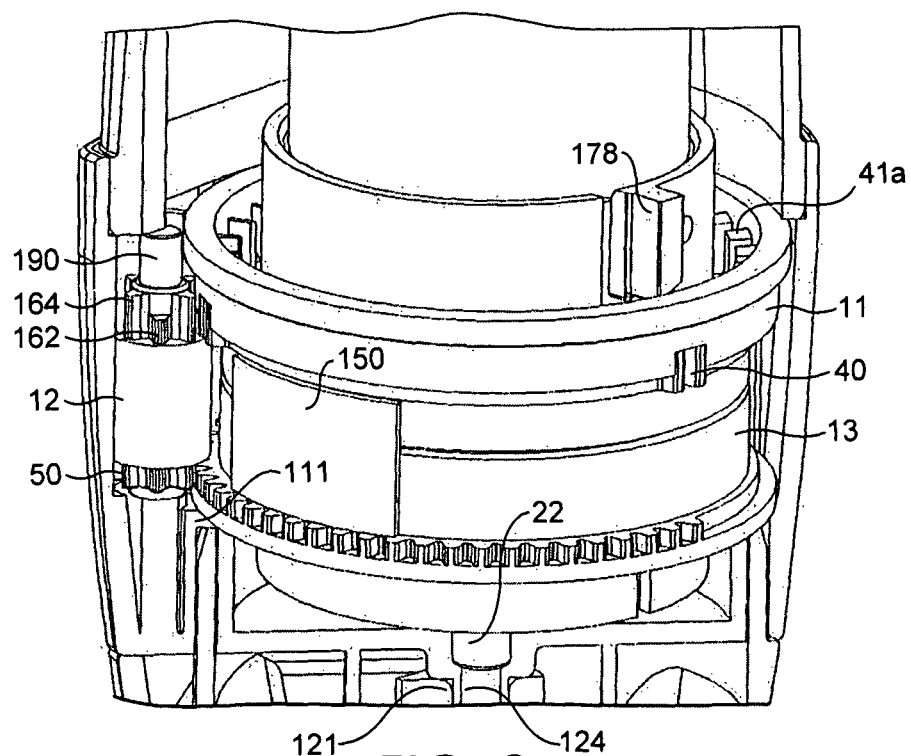
FIG. 3 is a perspective view of various internal features of the dispensing apparatus of FIG. 1.
Figures 5, 6:
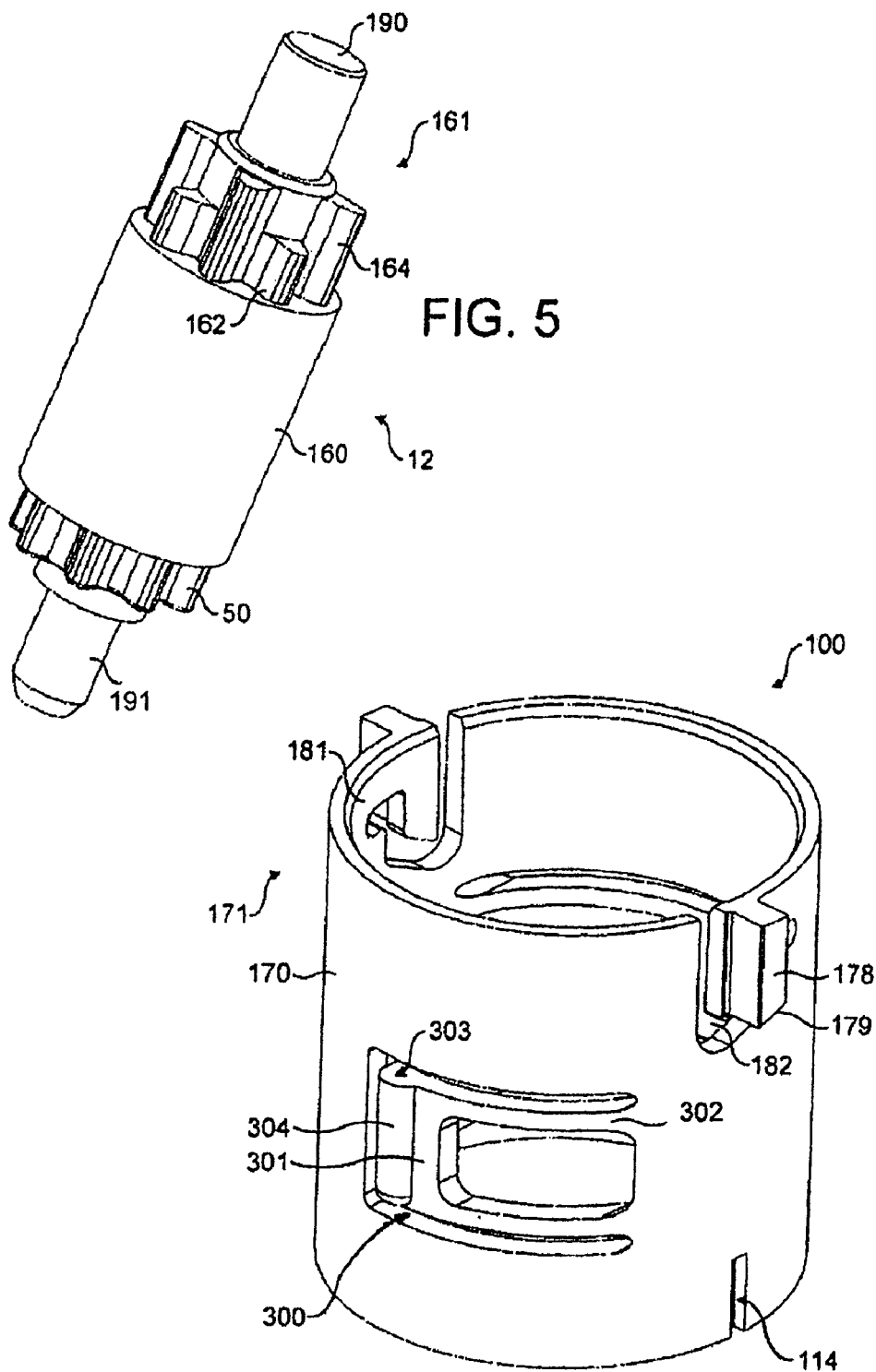
FIG. 5 is a perspective view of a cog forming part of the dispensing apparatus of FIG. 1.
FIG. 6 is a perspective view of a sleeve forming part of the dispensing apparatus of FIG. 1.

The cog 12, as shown in FIG. 5 in particular, is provided with one or more teeth separated by a non-toothed, cylindrical, spacer 160. A first end 161 of the cog 12 includes four teeth 162 of reduced height and four teeth 164 of full height which in use interact with the first annular member 11. The full height teeth 164 extend from the spacer 160 to the distal face of the first end 161 of the cog 12. The teeth 50 at a second end of the cog 12 are all full height and these teeth in use interact with the second annular member 13. The four teeth 162 having reduced height are, typically, half the height of the full height teeth 164. Most preferably, the reduced height teeth 162 and full height teeth 164 are arranged alternately around the circumference of the cog 12. The cog 12 is provided with upper and lower axial projections 190 and 191 which allow the cog 12 to be rotationally mounted in recesses formed in the lower body 5 as shown in FIG. 3.

As shown in FIGS. 2 and 6, the sleeve 100 comprises an opened-ended cylinder 170 having an upper end 171 which can receive the container 10 to be located in the dispensing apparatus 1 and a lower end 172 which has a reduced diameter opening 173 through which the valve stem 22 of the container 10, located within the sleeve 100 may protrude from but through which the body of the container 10 cannot pass. The sleeve 100 is provided with two sets of formations on its exterior surface. The sets of formations are arranged diametrically opposite one another (only on set of formations is shown in FIG. 6). Each set formations comprises first, second and third formations. The first formation is provided at the lower end 172 in the form of notches 114. The second formation is provided above the notches 114 in the form of a tension arm 300. The tension arm 300 comprises a cantilevered portion 301 which is fixed to the sleeve 100 at a hinge point 302. Preferably, the tension arm 300 is provided in a single moulding as part of the sleeve 100 in which case the hinge point 302 marks the junction between the body of the sleeve 100 and the start of the cantilevered portion 301 of the tension arm 300. A distal end 303 of the tension arm 300 is provided with an outwardly directed projection 304. It can be seen from FIG. 6 that the cantilevered tension arm 300 is able to accommodate flexure in a direction perpendicular to flexure of the cantilevered projection 178. That is, the outwardly directed projections 304 of the tension arm 300 can flex substantially radially inwards when pressure is applied to the projections in a radially inward direction. It will be appreciated that the shape of the container 10 must accommodate inward flexure of the tension arms 300. It is therefore preferable that the position of the tension arms 300 be located to coincide with the neck of the container 10 where it narrows to meet the ferrule of the meeting valve, thereby forming an undercut. Alternatively, the walls of the container 10 may have formed in them depressions to accommodate inward flexure of the tensions arms 300. The third formation is provided at the upper end 171 in the form of a cantilevered projection 178. The cantilever projection comprises an elongated portion having an angled abutment surface 179 on its lower, distal end. The elongated portion of the cantilevered projection 178 is axially aligned with the sleeve 100. The elongated portion is joined to the cylindrical body of the sleeve at a hinge point. The void space 182 is formed around the elongated portion to accommodate movement of the cantilevered projection 178 in use as will be described below.

The lower body 5 is provided with a clear portion 30, or one or more apertures 30 through which portions provided with markings of the number rings 11, 13 are visible. The upper body 3 is transparent to allow a user to easily see the type of container 10 located in the apparatus 1.

The opening in the upper body 3 is sized such that the sleeve 100 cannot pass therethrough but so that the container 10 is able to pass through.

In use, the internal components of the apparatus, such as the cog 12, the sleeve 100 and the number rings 11, 13 can be loaded into position within the apparatus 1 by separating the upper body 3 from the lower body 5. The cog, number rings and sleeve 100 can be inserted into the opening of the lower body 5. The internal projections 110 of the lower body 5 are received slidingly in the notches 114 of the sleeve 100 with the effect that the sleeve 100 is fixed rotationally relative to the lower body 5. The sleeve 100 is arranged to pass through the central holes/apertures of the number rings 11, 13. The upper body 3 is then attached to the lower body 5. The connection between the upper body 3 and lower body 5. The connection between the upper body 3 and lower body 5 may be designed to prevent easy further detachment of the two parts to thereby provide a tamper-resistant means of enclosing the container 10.

The pressurised dispensing container 10 can now be passed through the hole in the upper body 3 to be received in the sleeve 100. The valve stem 22 of the pressurised dispensing container 10 is received in the opening of the conduit 124 of the axial protrusion 121 as a relatively tight interference push-fit. When loaded, the number rings 11, 13 are located around the container 10 as shown in FIG. 3.

In the inserted position the upper end of the container 10 protrudes upwardly through the hole in the upper body 3 as shown in FIG. 1. Preferably, the container 10 only protrudes slightly above the level of the upper body 3. In the illustrated embodiment scallops 17 are provided in the upper edge of the upper body 3 and the container 10 protrudes above the level of the scallops but does not protrude above the highest part of the upper edge. The depth of the scallops 17 allows a user to depress the container 10 sufficiently to actuate the container's valve but reduces the area of the container 10 that can be gripped by the fingers of anyone attempting to remove the container 10 from the apparatus 1. Thus the amount of pulling force that can be applied to the container 10 is not enough to overcome the friction produced by the interference fit between the valve stem 22 and the conduit 124. Also, the fact that the container 10 does not protrude above the highest part of the upper edge helps to prevent accidental actuation of the apparatus when carried in the pocket. Advantageously, this mechanism of retaining the container 10 within the body portion can be used on its own without the need to provide an additional non-return feature.

The apparatus 1 is actuated by depression of the container 10 which protrudes above the scallops 17 of the upper body 3. Depression of the container 10 causes the container 10 and sleeve 100 to move axially within the main body 5 to actuate the container 10. Actuation causes an amount of product to be dispensed from the container 10 by an opposite reaction force from the constriction in the axial protrusion 121 acting on the valve stem 22, which is inwardly retracted relative to the remainder of the metering valve such that an amount of product is dispensed from the valve stem 22 through the conduit 124 and the valve stem receiving block 14, from where it is dispensed as an aerosol through the mouthpiece 20 and inhaled by a user inhaling on the mouthpiece 20. Release of the container 10 causes the container to return to its starting position, owing to the internal spring bias of the metering valve, ready for subsequent dispensing.

Each actuation of the apparatus 1 causes the first number ring 11 to rotate a partial increment during the downstroke of the dispensing container owing to engagement of the angled abutment surface 179 of the cantilevered projection 178 with the angled abutment surfaces 41a the first number ring 11. This rotation of the first number ring 11 causes each outwardly directed projection 304 of each tension arm 300 to ride up an angled face 311 of respective projections 310. This movement is accommodated by the tension arms 300 as they flex radially inwards. The relative location of the angled abutment surfaces 41a and the projections 310 is such that when the down stroke of the sleeve 100 is completed the outwardly directed projections 304 of the tension arms 300 have ridden up the angled abutment surfaces 311 and over the peak of the projections 310 such that the outwardly directed projections 304 lie in contact with the angled abutment surfaces 312 of the projections 310. Thus, when the container or cap is released, and the sleeve 100 consequently moves back on its up stroke, the completion of the incremental rotation of the first number ring 11 is achieved by the biasing force of the outwardly directed projections 304 of the tension arms 300 on the angled abutment surfaces 312 as the tension arms 300 try to return to their unstressed position. This biasing force completes the rotation of the first number ring 11 such that the outwardly directed projections 304 of the tension arms 300 lie in the neighbouring trough between the projections 310 after one actuation. Consequently, the cantilevered projection 178 and the tension arm 300 (or the pairs of these features where present) act as first and second indexing members which together act to index the counter mechanism.

Importantly, the force needed to rotate the first number ring 11 during a normal mode of operation is less than the force needed to flex the cantilevered projection 178 about the hinge point 181 sufficiently to allow the projection to bypass the teeth of the first number ring 11. Thus, normally the number ring 11 rotates rather than the cantilevered projection 178 being flexed.

Every ten actuations of the apparatus 1 cause the notch 40 to pass the cog 12, the effect of this being that one of the full height teeth 164 of the upper row of teeth is caught in the notch 40 as it rotates, this rotation causes a corresponding rotation of the cog 12 in the opposite sense. As a consequence, the second number ring 13 is caused to rotate in the same sense as the first number ring 11 by interaction of the teeth 50 on the bottom of the cog 12 and the teeth of the second number ring 13. Therefore, it can be seen that every actuation of the apparatus causes the value of the numbering visible through the one or more apertures 30 to be decreased or augmented by a value of one.

If the number rings 11, 13 or cog 12 become jammed or otherwise inoperative the dispensing apparatus can still be actuated as follows. On engagement of the angled abutment surface 179 of the cantilevered projection 178 against the angled surfaces 41a of the first number ring (which are now immobile) the elongated portion 180 of the cantilevered projection flexes about the hinge point 181 so that the distal end of the elongate portion 180 moves out of alignment with the angled surfaces 41a of the teeth of the first number ring. The cantilevered projection and hence the sleeve 100 as a whole can now move axially downwardly into the actuated position with the elongated portion 180 of the cantilevered projection passing between a pair of the teeth 41 of the first number ring 11.

Another advantage of the use of the cantilevered projection 178 for incrementing the indexing mechanism is that it provides the dispensing apparatus with a mechanism for resisting sudden impacts. With some conventional mechanical dosage counters a problem can occur where the dispensing apparatus is dropped or otherwise suffers a sudden impact. This can cause damage to the indexing mechanism, in particular to the relatively small and delicate teeth of the counter rings 11, 13 or cause the indexing mechanism to increment or decrement because the indexing member is held, in the unactuated position, in close proximity or in contact with the indexing mechanism. In the present invention the use of the cantilevered projection 178 provides a degree of inherent flexibility in the indexing member which allows the indexing member to absorb sudden impulses of force such as occur when the device is dropped without leading to damage of the mechanism or causing the annular members 11, 13 being incremented or decremented. For example if the dispensing apparatus is dropped so as to impact on a hard surface with the mouthpiece lowermost, the force impulse is transmitted upwardly through the lower body 5 into the annular members 11, 13. The force impulse is then transmitted from the annular members to the cantilevered projection 178. However, at this point the cantilevered projection 178 is able to flex upwardly sufficiently to absorb the impulse without the effect that the upper annular member is rotated relative to the cantilevered projection or damaged. Thus, the inherent flexibility of the cantilevered projection 178 and the fact that a void space 182 is provided around it to accommodate movement of the cantilevered projection 178, provides the dispensing apparatus with a mechanism for coping with impact forces without indexing the indexing mechanism or causing damage to the mechanism.

Whilst in the specific example details of the invention are discussed, it will of course be understood that minor variations in features are still considered to be covered by the same inventive concept.

In an alternative embodiment, the dispensing apparatus may comprise, say, three or more number rings: a first number ring for 'units', a second for 'tens' and a third for 'hundreds'. Further cogs may be provided. Subsequent number rings for 'thousands' and so on may also be added. The second and subsequent number rings are rotated by an arrangement as described herein (by a cog rotated by a previous number ring), whereby ten incremental rotations of the previous number ring—as started originally on the 'units' number ring by actuation of the apparatus—causes an incremental rotation of the subsequent number ring.

Figure 13:
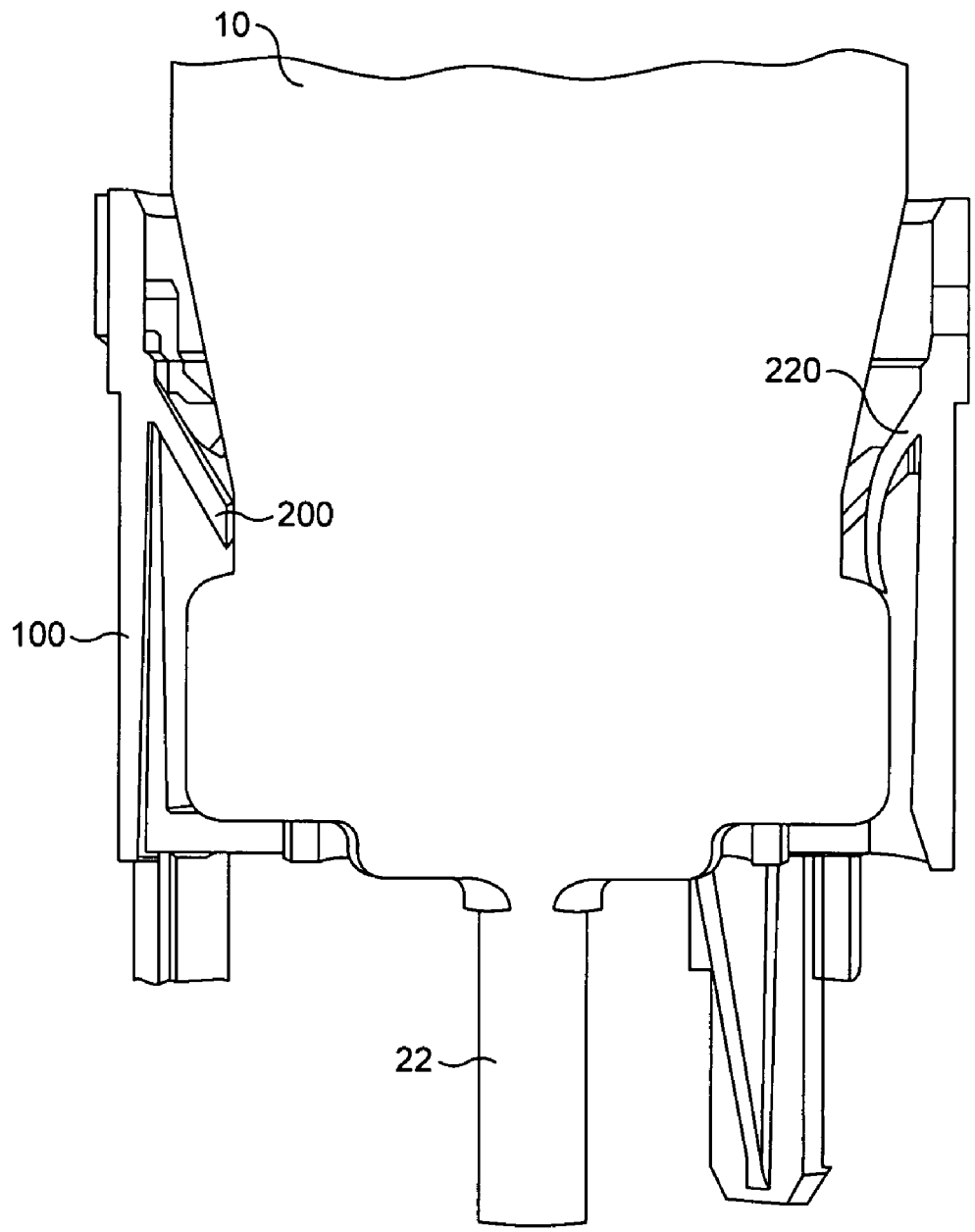
FIG. 13 is a schematic view part of an alternative part of the apparatus of FIG. 1.

FIG. 13 illustrates a modified arrangement wherein the sleeve 100 is additionally provided with one or more flexible legs 220 that depend from an inner face of the sleeve 100 and are directed downwardly at an angle towards a basal inner face of the sleeve 100 in which the lower opening is formed. The legs 220 are relatively flexible such that the container 10 can be fully inserted by flexing of the legs. The legs 220 serve two functions. Firstly they provide a 'snap-fit' arrangement to help ensure a positive loading action where full engagement of the container 10 with the sleeve 100 is made more consistent. This is achieved because the force required to flex the legs 220 out of the path of the container 10 ensures that the container 10 must be inserted into the sleeve with a minimum force. Once the container 10 has deflected the legs 220 out of its path the force applied to the container 10 acts to shoot home the container into abutment with the lower face of the sleeve. Secondly, the length and angle of the legs 220 act as a biasing mechanism to prevent slippage between the sleeve 100 and the container 10 when assembled whatever the orientation of the apparatus. As shown in FIG. 13, with the container fully engaged with its end face abutting the lower end face of the sleeve 100 the legs 220 are still flexed and in contact with the sloped undercut of the container 10 formed by crimping of the ferrule. Thus, the legs 220 bias the container 10 against the lower face of the sleeve 100.

Figure 9:
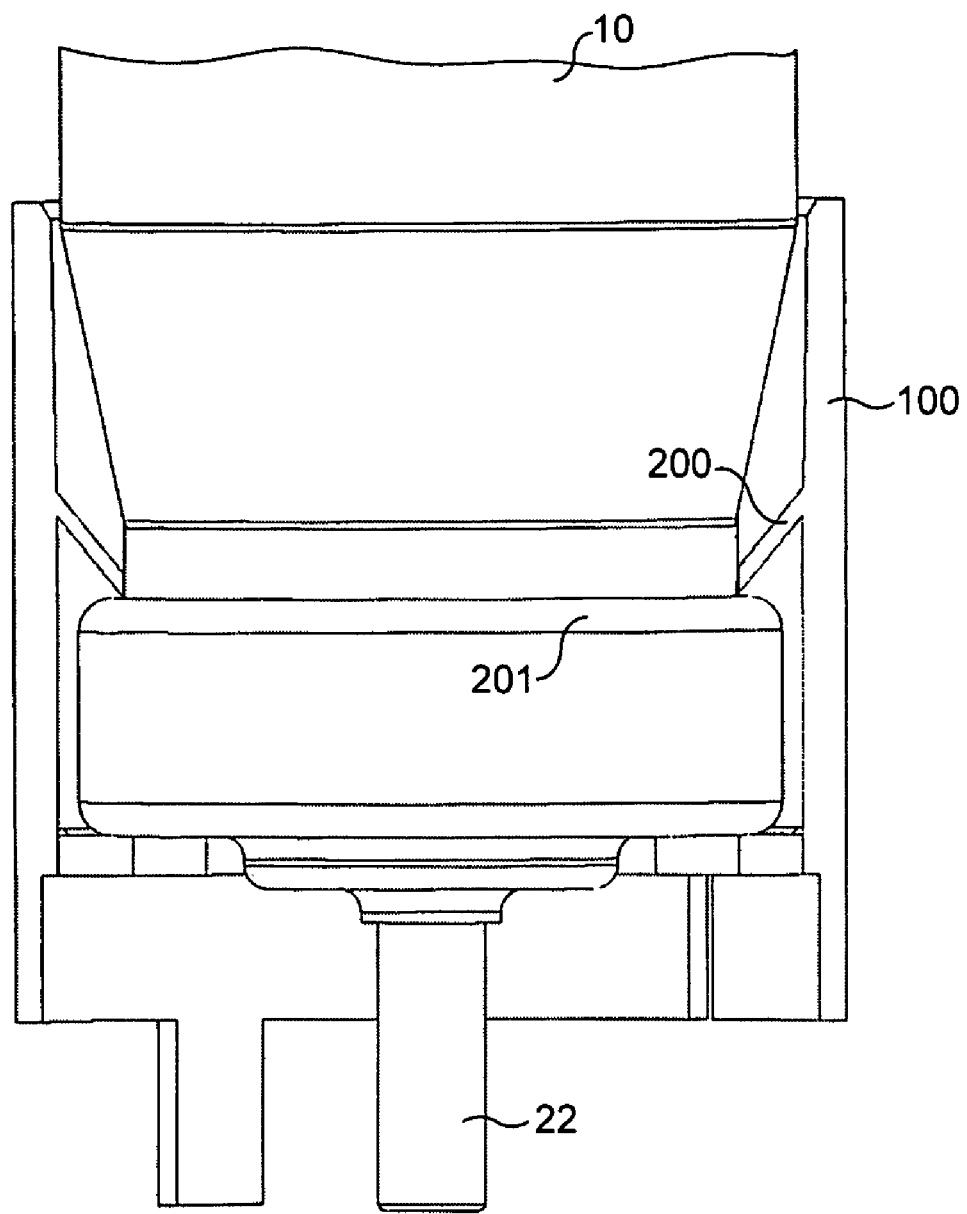
FIG. 9 is a schematic view of part of the apparatus of FIG. 1 with some parts omitted for clarity.

If desired the apparatus may be provided with a non-return feature in place of, or in addition to the interference fit between the valve stem 22 and conduit 124 as a means of retaining the container 10 within the housing. For example, the internal face of the sleeve 100 may be provided with a non-return feature 200, shown schematically in FIG. 9. The non-return feature 200 may be in the form of a flexible flange but is shown, and is preferably in the form of a pair of flexible legs 200 which protrude inwardly and in a downwards direction. As the container 10 is inserted into the sleeve 100 the legs 200 are deflected outwardly to allow a ferrule 201 of the container 10 to pass. Once in the assembled position the legs 200 spring back outwardly to engage in an undercut formation formed between the ferrule 201 and the body of the container 10 as shown in FIG. 9. Most preferably, the distal ends of the legs 200 engage at the internal point of inflection of the ferrule formed by the crimping of the ferrule as shown in FIG. 9. In this way removal of the container 10 from the sleeve 100 is prevented or made more difficult since the legs 200 will act as a strut when a pulling force is applied to the container 10. It is to be noted that the tightness of the grip between the legs 200 and the container 10 can be varied by varying the length and stiffness of the legs 200. The use of the legs 200 can be in combination with the use of the flexible legs 220 as shown in FIG. 13. Where such a combination is used the legs 200 and flexible legs 220 perform their separate functions as described above of, respectively, preventing or resisting removal of the container 10 from the sleeve 100 and biasing the container's end face against the basal face of the sleeve 100. Typically, the legs 200 will be less flexible than the flexible legs 220.

Figure 10:
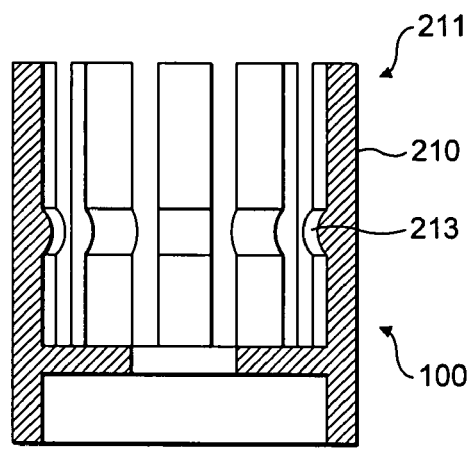
FIG. 10 is a schematic view of an alternative part of the apparatus of FIG. 1 with some parts omitted for clarity.

In an alternative arrangement shown in FIG. 10 the sleeve 100 (or an equivalent component) comprises a number of flexible fingers 210 which are connected to a body of the sleeve 100 at a lower end but free at an upper end 211. A number of the fingers 210, preferably alternate fingers, are provided with inward facing projections 213 which act as the non-return feature which engage the undercut formed between the ferrule 201 and body of the container 10. In use, the fingers 210 are able to flex sufficiently to allow the container 10 to be inserted into the sleeve 100. However, the lack of purchase on the container 10 caused by only a small part of the container protruding above the lower edge of the scallops results in it being relatively difficult to apply enough force to remove the container from the sleeve 100.

Figure 11:
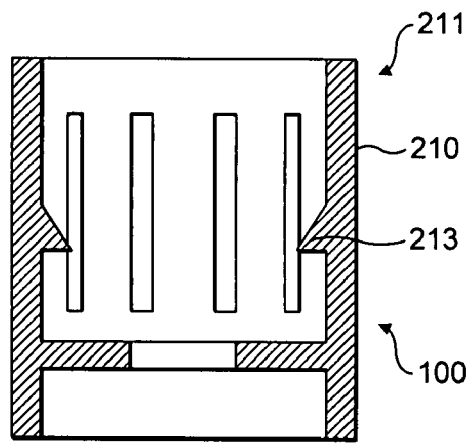
FIG. 11 is a schematic view of an alternative part of the apparatus of FIG. 1 with some parts omitted for clarity.

A further alternative is shown in FIG. 11 which is similar to the version in FIG. 10 except that the fingers 210 are joined together at their upper ends 211. It is also seen that the projection 213 takes the preferred form of having a ramped surface configuration which acts to ease insertion of the container 10 into the sleeve 100 but resists to a degree removal of the container 10. In use, the fingers 210 flex outwards in the middle to allow insertion of the container 10.

Figure 12:
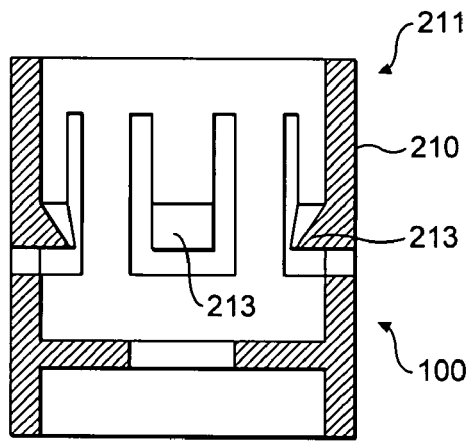
FIG. 12 is a schematic view of an alternative part of the apparatus of FIG. 1 with some parts omitted for clarity.

FIG. 12 shows a further alternative wherein the fingers 210 are joined to the body of the sleeve 100 at their upper ends but are free to flex at their lower ends. Functionally the three arrangements work similarly.

The invention claimed is:

1. A dispensing apparatus for delivering metered doses of product from a pressurised dispensing container comprising:
   a housing comprising a body portion and a removable mouthpiece, the body portion containing a dose counting mechanism and a sleeve;
   the body portion comprising an aperture through which a pressurised dispensing container can pass to be received in the sleeve but through which the sleeve is unable to pass such that the sleeve is retained within the body portion;
   the sleeve being located in the body portion such that an upper end of a pressurised dispensing container, when received in the sleeve, is accessible to allow actuation of said pressurised dispensing container; and
   the apparatus comprising means for retaining said pressurised dispensing container in the body portion and a biasing mechanism for urging, on insertion of said pressurised dispensing container into the sleeve, an end face of a body of the pressurised dispensing container into positive engagement contact with a basal face of the sleeve.

2. The dispensing apparatus as claimed in claim 1 wherein the means for retaining said pressurised dispensing container in the body portion comprises an opening in the body portion dimensioned to receive a valve stem of said pressurised dispensing container as an interference fit.

3. The dispensing apparatus as claimed in claim 2 wherein the opening in the body portion is a part of a conduit for conveying a product dispensed from the valve stem of the pressurised dispensing container to the removable mouthpiece.

4. The dispensing apparatus as claimed in claim 1 wherein the biasing mechanism comprises one or more flexible projections on the sleeve which are engagable with said pressurised dispensing container.

5. The dispensing apparatus as claimed in claim 4 wherein the one or more flexible projections depend from an inner face of the sleeve and are directed towards a basal face of the sleeve.

6. The dispensing apparatus as claimed in claim 4 wherein the one or more flexible projections are engagable in an undercut of said pressurised dispensing container formed by a ferrule of said pressurised dispensing container.

7. The dispensing apparatus as claimed in claim 1 wherein the means for retaining said pressurised dispensing container in the body portion is dimensioning the sleeve such that an interference fit is produced between said pressurised dispensing container and the sleeve.

8. The dispensing apparatus as claimed in claim 1 wherein a surrounding of the aperture of the body portion comprises one or more scallops which allow access to said pressurised dispensing container in order to actuate said pressurised dispensing container, but which limit the available purchase on said pressurised dispensing container.

9. The dispensing apparatus as claimed in claim 1 wherein the dose counting mechanism comprises indication means for displaying to a user an indication associated with the number or quantity of doses dispensed from, or the number or quantity of doses remaining in, said pressurised dispensing container.

10. The dispensing apparatus as claimed in claim 1 wherein the sleeve comprises an indexing member for advancing the dose counting mechanism on actuation of said pressurised dispensing container.

11. The dispensing apparatus as claimed in claim 1 wherein the removable mouthpiece comprises a bayonet fitting mechanism.

12. The dispensing apparatus as claimed in claim 1 wherein the dose counting mechanism comprises one or more annular members.

13. The dispensing apparatus as claimed in claim 12 wherein the one or more annular members are orientated for rotation about the longitudinal axis of the housing.

14. The dispensing apparatus as claimed in claim 13 wherein, in use, said pressurised dispensing container is received within the housing such that the one or more annular members surround said pressurised dispensing container.

15. The dispensing apparatus as claimed in claim 1 wherein the body portion comprises a lower part and an upper part.

16. The dispensing apparatus as claimed in claim 1 wherein the body portion is formed from Polycarbonate, acrylonitrile butadiene styrene, Polypropylene, co-polyester or high-density polyethylene.

17. The dispensing apparatus as claimed in claim 1 wherein the sleeve is formed from acetal, acrylonitrile butadiene styrene or nylon.

18. A dispensing assembly comprising a dispensing apparatus as claimed in claim 1 and a pressurised dispensing apparatus.

19. A dispensing apparatus for delivering metered doses of product from a pressurised dispensing container comprising:

a housing comprising a body portion and a removable mouthpiece, the body portion containing a dose counting mechanism and a sleeve;

the body portion comprising an aperture through which a pressurised dispensing container can pass to be received in the sleeve but through which the sleeve is unable to pass such that the sleeve is retained within the body portion;

the sleeve being located in the body portion such that an upper end of a pressurised dispensing container, when received in the sleeve, is accessible to allow actuation of said pressurised dispensing container; and the apparatus comprising means for retaining said pressurised dispensing container in the body portion and a biasing mechanism for urging, on insertion of said pressurised dispensing container into the sleeve, said pressurised dispensing container into positive engagement with the sleeve, wherein the means for retaining said pressurised dispensing container in the body portion is a non-return feature provided on the sleeve.

20. The dispensing apparatus as claimed in claim 19 wherein the non-return feature comprises an inwardly directed flange of the sleeve which allows a pressurised dispensing container to pass thereby on insertion of said pressurised dispensing container but acts to resist or prevent subsequent withdrawal of said pressurised dispensing container from said sleeve.

21. The dispensing apparatus as claimed in claim 19 wherein the non-return feature comprises one or more inwardly directed projections which allow said pressurised dispensing container to pass thereby on insertion of said pressurised dispensing container but acts to resist or prevent subsequent withdrawal of said pressurised dispensing container from said sleeve.

22. The dispensing apparatus as claimed in claim 21 wherein the one or more inwardly directed projections comprises a plurality of flexible fingers which are free at one end.

23. The dispensing as claimed in claim 21 wherein the one or more inwardly directed projections comprises a plurality of flexible fingers which are joined or formed as one with the sleeve at an upper and lower end of the fingers.

24. The dispensing apparatus as claimed in claim 19, wherein the biasing mechanism is provided on the sleeve.

* * * * *